US009988211B1

(12) United States Patent
Just et al.

(10) Patent No.: US 9,988,211 B1
(45) Date of Patent: Jun. 5, 2018

(54) LOCKABLE MOUNTING BRACKET (71) Applicant: Stericycle, Inc., Northbrook, IL (US)

(72) Inventors: Lyndon Jay Just, Elgin, IL (US);
James Lawrence Fitch, Lake in the Hills, IL (US); Brian Foos, Roselle, IL (US)

(73) Assignee: STERICYCLE, INC., Northbrook, IL (US)

( * ) Notice: Subject to any disclaimer, the term of this patent is extended or adjusted under 35 U.S.C. 154(b) by 0 days. days.

(21) Appl. No.: 15/597,046

(22) Filed: May 16, 2017

(51) Int. Cl.
B65F 1/14 (2006.01)
F16M 13/02 (2006.01)
F16B 2/10 (2006.01)
B65F 1/00 (2006.01)

(52) U.S. Cl.
CPC ............ B65F 1/141 (2013.01); F16B 2/10 (2013.01); F16M 13/02 (2013.01); B65F 1/0066 (2013.01); B65F 1/1415 (2013.01); B65F 1/1426 (2013.01); F16M 2200/028 (2013.01)

(58) Field of Classification Search
CPC ...... B65F 1/141; B65F 1/1415; B65F 1/1421; B65F 1/1426; B65F 1/0013; B65F 1/0066; B65F 1/0073; F16M 13/02; F16M 2200/028; F16M 2200/00; F16M 2200/06; F16M 2200/02; A47K 1/08; F16B 2/10
USPC .... 248/312, 312.1, 311.2, 309.1, 313, 316.1, 248/316.5, 316.6, 311.3; 24/573.1, 339, 24/279, 456
See application file for complete search history.

(56) References Cited

U.S. PATENT DOCUMENTS

| 1,210,102 A | * | 12/1916 | De Riggins | A47G 29/24 232/41 E |
| 2,754,009 A | * | 7/1956 | Kennedy | A47J 47/16 211/74 |
| 4,828,107 A | | 5/1989 | Spencer | |
| 4,905,950 A | * | 3/1990 | Turner | A62C 13/78 24/273 |

(Continued)

OTHER PUBLICATIONS

Med on the Go.com, "Wire Bracket for 3 Gal Sharps Container Wall Mount Locking 8786F," <http://www.medonthego.com/Wire-Bracket-for-3-Gal-Sharps-Container-Wall-Mount-Locking-8786F-1-Ea_p_131095.html> website accessed Mar. 1, 2017 (3 pages).

(Continued)

Primary Examiner — Nkeisha Smith
(74) Attorney, Agent, or Firm — Michael Best & Friedrich LLP (57) ABSTRACT A mounting bracket for mounting a container to a support surface includes a base having a mounting portion configured to be mounted to the support surface and a support portion configured to receive a portion of the container. The bracket further includes a securing member pivotally coupled to the support portion for movement in only a single pivot plane between a first position, in which the container can be removed from the support portion, and a second position, in which the container cannot be removed from the support portion. A lock is operable to selectively lock the securing member in the second position. At least one of the base or the securing member includes an aperture through which a portion of the other one of the base or the securing member extends when the securing member is in the second position.

21 Claims, 5 Drawing Sheets

(56) References Cited

U.S. PATENT DOCUMENTS

| | | | | |
|---|---|---|---|---|
| 4,955,574 | A * | 9/1990 | Freier | F16L 3/1203 248/316.5 |
| 5,058,764 | A | 10/1991 | Gaba | |
| 5,071,100 | A * | 12/1991 | Sweeny | A62C 13/78 248/310 |
| 5,098,054 | A * | 3/1992 | Dyer | F16B 2/08 248/225.11 |
| 5,103,997 | A * | 4/1992 | Shillington | B65F 1/141 206/366 |
| 5,344,112 | A * | 9/1994 | Peterson | B60H 1/3229 24/279 |
| 5,423,508 | A | 6/1995 | Isenga et al. | |
| 5,472,167 | A | 12/1995 | Shillington et al. | |
| 5,572,776 | A * | 11/1996 | Murphy | F16B 2/10 24/487 |
| 5,601,268 | A | 2/1997 | Dunchock | |
| 5,971,335 | A | 10/1999 | Perrin et al. | |
| 6,059,245 | A * | 5/2000 | Hermansen | B62J 11/00 248/311.2 |
| 6,138,960 | A * | 10/2000 | Carbonare | F16L 3/1083 248/62 |
| 6,357,713 | B1 | 3/2002 | BeBow | |
| 6,830,226 | B2 * | 12/2004 | Field | A62B 25/00 248/313 |
| 6,837,472 | B1 | 1/2005 | Beutz | |
| 7,234,673 | B2 | 6/2007 | Graneto, III | |
| 9,146,003 | B2 * | 9/2015 | Carson | F16M 13/02 |
| 9,278,238 | B2 * | 3/2016 | Thau, Jr. | F16B 2/10 |
| 2004/0149878 | A1 | 8/2004 | Gierke et al. | |
| 2011/0260012 | A1 * | 10/2011 | Oh | A62C 35/68 248/89 |
| 2011/0284098 | A1 * | 11/2011 | Silcox | A62C 35/68 137/15.18 |
| 2013/0048822 | A1 * | 2/2013 | Liu | F16B 2/10 248/316.5 |
| 2013/0105641 | A1 * | 5/2013 | Feenstra | A62C 35/68 248/75 |

OTHER PUBLICATIONS

Staples.com, "Kendall/Covidien Sharps Containers; Locking Bracket 2 Gal." <http://www.staples.com/Kendall-Covidien-Sharps-Containers-Locking-Bracket-2-Gal-/product_541182> website accessed Feb. 28, 2017 (3 pages).

Stericycle.com, "Stericycle Mailback Wall Bracket," < https://store.stericycle.com/stericycle-mailback-wall-bracket/mbbrkt/> website accessed Feb. 23, 2017 (5 pages).

Stericycle.com, "BD Locking Wall Bracket" <https://store.stericycle.com/bd-locking-wall-bracket/305409-p/> website accessed Feb. 28, 2017 (3 pages).

* cited by examiner

LOCKABLE MOUNTING BRACKET

BACKGROUND

The present invention relates to mounting brackets, and more particularly to mounting brackets for medical waste containers.

Containers of many types are often mounted to a wall or other support surface using brackets. For medical waste containers, such brackets are often lockable.

SUMMARY

In one aspect, the invention provides a mounting bracket for mounting a container to a support surface. The mounting bracket includes a base having a mounting portion configured to be mounted to the support surface and a support portion configured to receive a portion of the container. The bracket further includes a securing member pivotally coupled to the support portion for movement in only a single pivot plane between a first position, in which the container can be removed from the support portion, and a second position, in which the container cannot be removed from the support portion. A lock is operable to selectively lock the securing member in the second position. At least one of the base or the securing member includes an aperture through which a portion of the other one of the base or the securing member extends when the securing member is in the second position.

In another aspect the invention provides a mounting bracket including a base having a mounting portion configured to be mounted to the support surface, and a support portion configured to receive a portion of the container. The bracket further includes a securing member pivotally coupled to the support portion for movement between a first position, in which the container can be removed from the support portion, and a second position, in which the container cannot be removed from the support portion. A lock is operable to selectively lock the securing member in the second position. The base includes a flange with an aperture through which a portion of the securing member extends when in the second position, and the securing member includes a flange with an aperture through which a portion of the base extends when the securing member is in the second position.

In yet another aspect, the invention provides a mounting bracket including a base having a mounting portion configured to be mounted to the support surface and a support portion configured to receive a portion of the container. The bracket further includes a securing member pivotally coupled to the support portion between a first position, in which the container can be removed from the support portion, and a second position, in which the container cannot be removed from the support portion. A lock is operable to selectively lock the securing member in the second position. The securing member includes a notch and the lock includes a pawl that selectively engages the notch to lock the securing member in the second position and disengages the notch to allow the securing member to move out of the second position. The support portion includes a slot and the pawl extends into the slot when the pawl engages the notch.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. Use of relative terms such as "front," "rear," "side," "up," "down," "inside," "outside," "vertical," "horizontal," "above," "below" and the like, as well as derivatives of such terms (e.g., "vertically" and "horizontally"), should be construed to refer to exemplary orientation as then described or as shown in the drawing under discussion. These relative terms are for convenience of description and do not require that the apparatus be constructed or operated in a particular orientation. The invention is capable of other embodiments and of being practiced or of being carried out in various ways.

Figure 1:
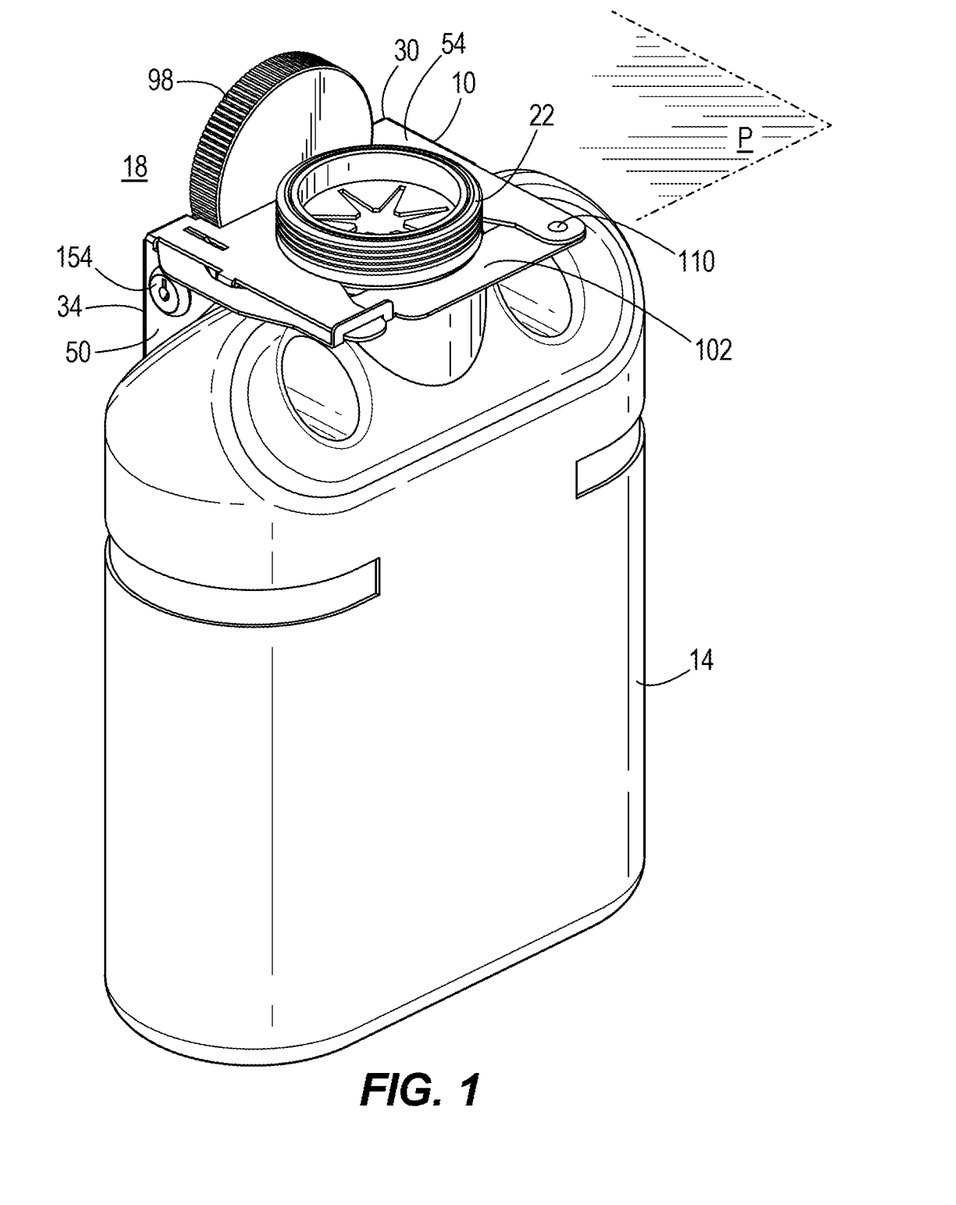
FIG. 1 is a front perspective view of a mounting bracket embodying the invention supporting a medical waste container.
Figure 2:
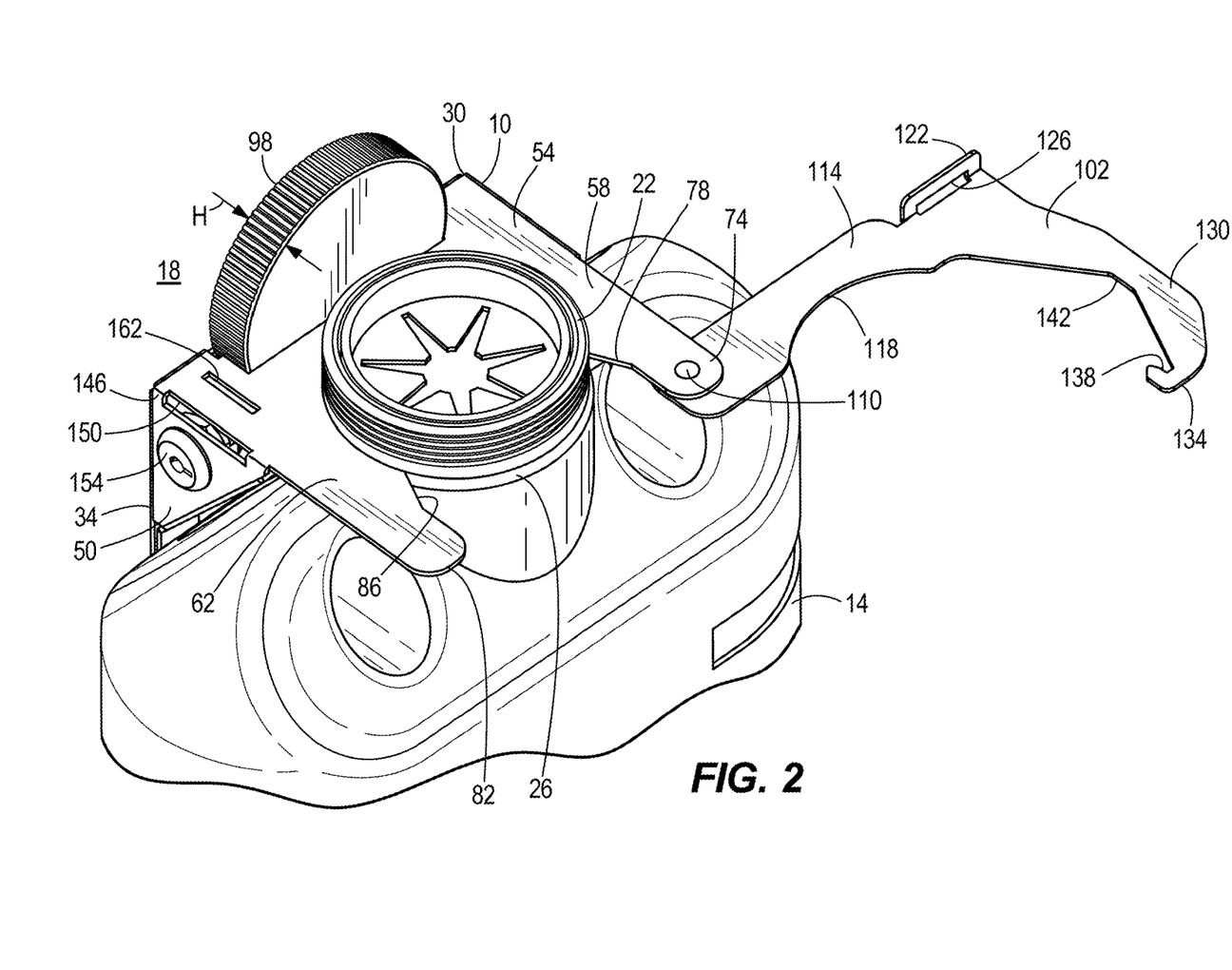
FIG. 2 is an enlarged partial front perspective view like FIG. 1, showing the mounting bracket in a first position in which it can receive or release the medical waste container.
Figure 3:
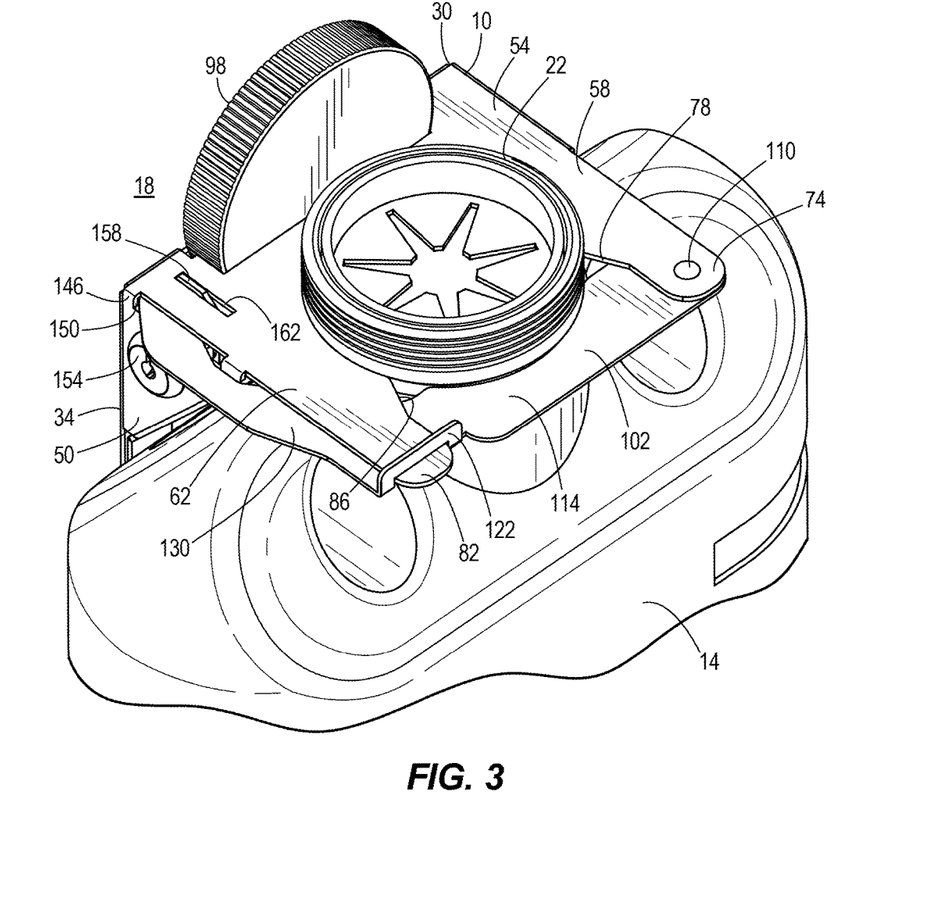
FIG. 3 is an enlarged partial front perspective view like FIG. 1, showing the mounting bracket in a second position in which it secures the medical waste container.

FIGS. 1-7 illustrate a mounting bracket 10 embodying the present invention. As shown in FIGS. 1-3, the mounting bracket 10 is illustrated as mounting a medical waste container 14 to a support surface 18 (e.g., a wall), however, in other embodiments, the mounting bracket 10 can be used to mount other types of containers to walls or various other support surfaces. The illustrated container 14 is one of many differently sized and shaped containers 14 that could be supported and secured by the bracket 10.

The container 14 includes a neck 22 sized and configured to be supported, retained and secured by the bracket 10. Those of skill in the art can understand how the shape of the container 14 might be changed, while keeping the configuration of the neck 22 the same, in order to enable the bracket 10 to work with various other container configurations. The illustrated container 14 includes a groove 26 (see FIG. 2) formed in the neck 22 for engagement with the bracket 10, as will be discussed further below.

The bracket 10 includes a base 30 having a mounting portion 34 (see FIGS. 4-7) configured to be mounted to the support surface 18. In the illustrated embodiment, the mounting portion 34 includes a first, vertically-oriented portion 38 having one or more apertures 42 for receiving fasteners (not shown) that secure the bracket 10 to the support surface 18. The vertically-oriented portion 38, when mounted to the support surface 18, is parallel to the support surface 18. The mounting portion 34 further includes second and third rib portions 46, 50 that extend away from the vertically oriented portion 38 (and from the support surface 18) to a support portion 54 of the bracket 10. The illustrated support portion 54 is oriented to be perpendicular to the vertically-oriented portion 38 of the mounting portion 34, and the second and third rib portions 46, 50 provide strength and rigidity to the bracket 10 to preserve the generally perpendicular orientation between the vertically-oriented portion 38 of the mounting portion 34 and the horizontally-oriented support portion 54. In the illustrated embodiment, the rib portions 46, 50 include respective flange portions 46*a* and 50*a* (see FIG. 7) extending generally inwardly from the respective rib portions 46, 50 to further add to the rigidity of the bracket 10, and in some embodiments, to provide an abutment against which portions of the container engage 14.

The support portion 54 is configured to receive a portion of the container 14. The support portion 54 is generally planar and includes a first arm portion 58 and a second arm portion 62 spaced apart from the first arm portion 58 to define therebetween a recess 66 into which the neck 22 of the container 14 is received. The recess 66 is sized and configured to snugly receive and accept the neck 22. In the illustrated embodiment, the support portion 54 has a thickness such that an edge 70 of the support portion 54 defining the perimeter of the recess 66 is sized and configured to be received in the groove 26 formed in the neck 22 to support the container 14 within the recess 66. In other embodiments, the container might alternatively include a flange or other structure instead of the groove 26 that engages with the support portion 54 in the vicinity of the recess 66. In yet other embodiments, no inter-engaging structure apart from the edge 70 and a smooth outer surface of the neck 22 may be present.

The first arm portion 58 includes a distal end 74 that is spaced from the vertically-oriented portion 38, and in the illustrated embodiment, is rounded or arcuate in shape. An angled or tapered transition portion 78 is formed on the first arm portion 58. Likewise, the second arm portion 62 includes a distal end 82 that is spaced from the vertically-oriented portion 38, and in the illustrated embodiment, is also rounded or arcuate in shape. An angled or tapered transition portion 86 is formed on the second arm portion 62. Together, distal ends 74 and 82 and the angled transition portions 78 and 86 define a widened entry or lead-in opening 90 (see FIG. 4) to the recess 66 that can help guide and facilitate entry of the neck 22 into the recess 66.

The support portion 54 further includes an aperture 94 sized and configured to receive and support a cover 98 of the container 14 when the container 14 is received in the bracket 10 for use. In the illustrated embodiment, the aperture 94 is adjacent to the vertically-oriented portion 38 and has a width W (see FIG. 5) that is slightly larger than a height H (see FIG. 2) of the cover 98 and a length L (see FIG. 5) that is slightly shorter than the diameter of the cover 98. With this configuration, the cover 98 can be inserted into the aperture 94 from above the support portion 54 but cannot pass entirely through the support portion 54. The aperture 94 provides convenient and accessible storage for the cover 98 such that it can be easily removed from the neck 22 yet kept nearby, and placed back onto the neck 22 as desired.

Figure 4:
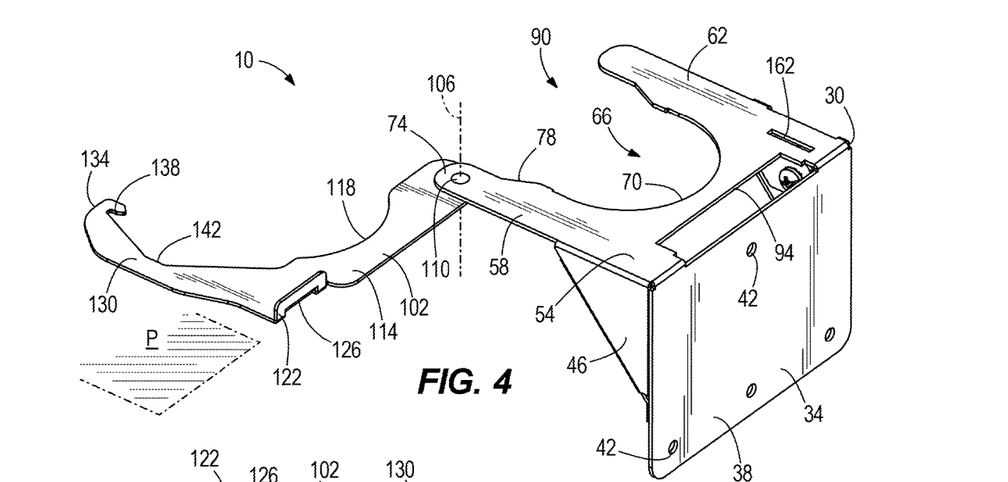
FIG. 4 is a rear perspective view of the mounting bracket of FIG. 1, shown in the first position without the medical waste container.
Figure 5:
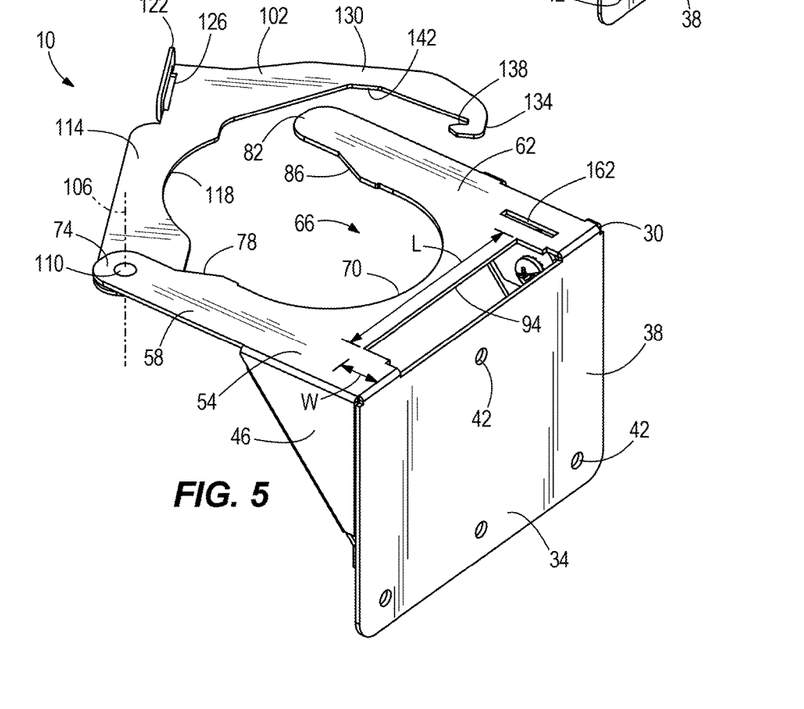
FIG. 5 is a perspective view taken from the right side of the mounting bracket of FIG. 1, shown in transition between the first and second positions.

The bracket 10 further includes a securing member 102 pivotally coupled to the support portion 54 for movement in only a single pivot plane P between a first position (see FIGS. 2 and 4), in which the container 14 can be removed from the support portion 54, and a second position (see FIGS. 3 and 6), in which the container 14 cannot be removed from the support portion 54. The securing member 102 is pivotally coupled to the distal end 74 of the first arm portion 58 about a pivot axis 106. In the illustrated embodiment, the pivotal connection is formed via a riveted, pinned or otherwise fixed and permanent structure 110 so that the securing member 102 is inseparable from the base 30. Therefore, the securing member 102 is constrained for rotation about the pivot axis 106 entirely within the pivot plane P (e.g., a horizontal plane as illustrated in FIGS. 1 and 4), and does not and cannot rotate or pivot in a vertical plane, or be lifted or lowered relative to the pivot plane P. In the illustrated embodiment, the securing member 102 is positioned beneath the support portion 54 as shown, however, in other embodiments, the bracket 10 could be configured such that the securing member 102 is positioned above the support portion 54.

Figure 6:
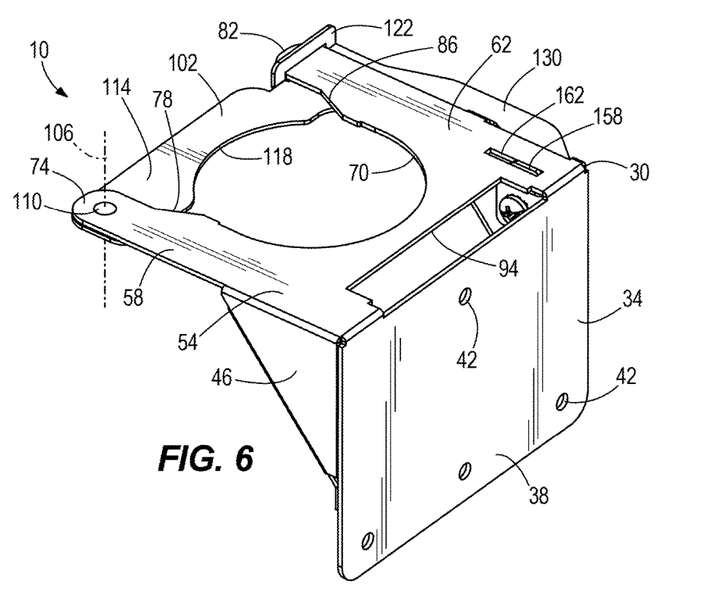
FIG. 6 is a perspective view taken from the right side of the mounting bracket of FIG. 1, shown in the second position.

The illustrated securing member 102 includes a first or front leg portion 114 extending from the distal end 74 of the first arm portion 58 to the distal end 82 of the second arm portion 62 when in the closed second position (see FIGS. 3 and 6). The front leg portion 114 is contoured along an inside edge 118 so as to receive and engage a portion of the neck 22 when the container 14 is received in the recess 66. In the illustrated embodiment, the securing member 102 has a thickness such that the edge 118 is sized and configured to be received in the groove 26 formed in the neck 22 to further support the container 14. Once again, in other embodiments, the container 14 might alternatively include a flange or other structure instead of the groove 26 that engages with the inside edge 118 of the securing member 102. In yet other embodiments, no inter-engaging structure apart from the edge 118 and a smooth outer surface of the neck 22 may be present and the container 14 might be held in place within the recess 66 by a clamping force applied by the securing member 102 when in the second position.

The securing member 102 further includes a flange 122, which in the illustrated embodiment, is located at an opposite end of the front leg portion 114 from the end that is pivotally connected to the distal end 74 of the first arm portion 58. The illustrated flange 122 is formed by a bent or formed-up portion of the outside edge of the front leg portion 114 and defines therein an aperture 126 through which a portion of the base 30 extends when the securing member 102 is in the second position. More specifically, when the securing member 102 is in the second position, the distal end 82 of the second arm portion 62 is received in and extends through the aperture 126 in the flange 122 of the securing member 102. When the distal end 82 is received in the aperture 126, the edges of the flange 122 that define the aperture 126 closely surround the distal end 82 on both lateral sides, as well as on the upper and lower sides. This arrangement provides a second location of constrained engagement between the base 30 and the securing member 102 when the securing member is in the second position, with the first location of constrained engagement being the pivotal connection at connecting structure 110. In this manner, there are locations of constrained engagement at both distal ends 74 and 82, and thus on both sides of the recess 66, to add to the security and robustness of the bracket 10 when securing the container 14 therein.

The securing member 102 further includes a second or side leg portion 130 that extends generally perpendicularly from the end of the front leg portion 114 that includes the flange 122. Together, the front and side leg portions 114 and 130 form a generally J-shaped or backward L-shaped arrangement. The side leg portion 130 includes a distal end 134 having a notch 138 formed therein. In the illustrated embodiment, the distal end 134 is formed in a hook-shaped configuration to define therein the notch 138. An inside edge 142 of the side leg portion 130 is generally V-shaped as shown (see e.g., FIG. 2).

Figure 7:
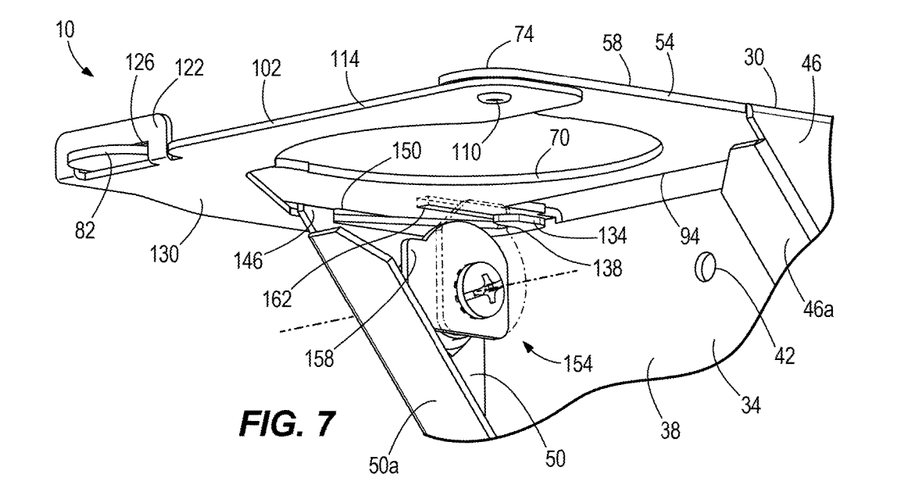
FIG. 7 is a partial perspective view from beneath the mounting bracket, illustrating the operation of the lock.

The intersection or interface between the support portion 54 and the third rib portion 50 defines a flange portion 146 having an aperture 150 through which a portion of the securing member 102, and specifically the distal end 134 of the securing member 102, extends when the securing member 102 is in the second position (see FIGS. 2, 3, and 7). The flange portion 146 can be considered to be the location where the third rib portion 50 is bent or formed downwardly from the support portion 54. The aperture is defined by an upper edge of the third rib portion 50, the side edge of the support portion 54, and the opposing facing edges of the bent interfaces (i.e., the flange portion 146) between the support portion 54 and the third rib portion 50. This arrangement provides a third location of constrained engagement between the base 30 and the securing member 102 when the securing member is in the second position. The vertex or valley in the inside edge 142 of side leg portion 130 provides clearance to allow the distal end 134 to extend into and through the aperture 150. In this manner, at least a portion of the flange portion 146 can engage the inside edge 142 of the side leg portion 130 and act as a stop defining when the securing member 102 is completely pivoted to the second position. In other embodiments, there could be clearance between the flange portion 146 and the inside edge 142 with the second position being instead limited by the engagement between the inside edge 118 of the front leg portion 114 and the neck 22 of the inserted container 14.

The bracket 10 further includes a lock 154 operable to selectively lock the securing member 102 in the second position. The illustrated lock 154 is a keyed cylinder lock having a pawl 158 (see FIGS. 3 and 7) that is rotatable upon rotation of a key in the lock 154 between a locked and an unlocked state. When the securing member 102 is in the second position and the lock 154 is rotated to the locked state, the pawl 158 engages the notch 138 (shown in phantom lines in FIG. 7) to lock the securing member 102. When the lock 154 is rotated to the unlocked state, the pawl 158 disengages the notch 138 (shown in solid lines in FIG. 7) to allow the securing member 102 to move out of the second position. As best shown in FIGS. 2, 3, and 7, the support portion 54 includes a slot 162 and the pawl 158 extends into the slot 162 when the pawl 158 engages the notch 138. This arrangement provides added security and robustness to the bracket 10 in that the pawl 158 not only engages the notch 138 in the securing member 102, but the pawl 158 also engages the slot 162 in the support member 54, thereby placing the pawl 158 into a double-shear arrangement that would be more difficult to defeat using a pry bar, screwdriver, or other tool. This arrangement provides a fourth location of constrained engagement between the base 30 and the securing member 102. Additionally, the arrangement and inter-engagement between each of the securing member 102, the support portion 54, the third rib portion 50 and the flange portion 146 eliminate any obvious location at which a pry bar or screwdriver could be inserted in an attempt to open the locked bracket 10 in an unauthorized manner.

In the illustrated embodiment, the lock 154 is supported in the third rib portion 50 of the mounting portion 34 of the base 30, with the cylinder of the lock 154 being secured in an aperture formed in the third rib portion 50. In other embodiments, the entire configuration of the bracket 10 could be reversed so instead of swinging open from left to right as in the illustrated embodiment, the bracket 10 could swing open from right to left. This would only require a simple reversal of the components.

The illustrated lock 154 is only one example of a lock 154 that could be used with the bracket 10. In other embodiments, a keyed pushbutton lock could be used with a pawl that is biased to the locked state, but that could be automatically moved to the unlocked state by engagement with the hook-shaped distal end 134 as it extends through the aperture 150. Once the securing member 102 reaches the second position, the pawl would be biased into the notch 138 and further into the slot 162. Then the key could be used to lock the pawl in this locked state. To unlock the securing member 102, the key could be used to turn the lock to the unlocked state, thereby retracting the pawl against the spring bias and out of the slot 162 and the notch 138. This arrangement is sometimes referred to as a slam-lock.

In the illustrated embodiment, each of the base 30 and the securing member 102 are formed of sheet metal having a thickness that permits portions of the base 30 (e.g., the edge 70) and the securing member 102 (e.g., the inside edge 118) to fit within the groove 26 in the neck 22 of the container when the securing member 102 is in the second position. The base 30 and the securing member 102 can be economically formed by stamping and bending the sheet metal to the final configurations shown in the illustrated embodiment.

The method of installing a container 14 into the bracket 10 will now be described. First, the bracket 10 can be secured to the wall or other support surface 18 by driving fasteners through the apertures 42 in the vertically-oriented portion 38 and into the wall 18 at the desired location at which the bracket 10 is to be mounted. Next, the securing member 102 is moved to the first position, thereby opening or exposing the recess 66 and the lead-in opening 90 for insertion of the neck 22 of the container 14. The neck 22 can be inserted into the lead-in opening 90 and further into the recess 66, taking care to align the groove 26 in the neck with the edge 70 defining the recess 66 so that the edge 70 enters the groove 26 to support the container 14 in the vertical direction. Once the container 14 is fully installed into the recess 66, with the edge 70 received in the groove 26, the securing member 102 can be pivoted from the first position toward the second position. Once again, in the illustrated embodiment, the securing member 102 is constrained for movement (e.g., rotation) in only the single plane P and need not be lifted, pivoted, or otherwise moved in a second direction relative to the pivot axis 106.

When container 14 is installed into recess 66, the container 14 will cover the apertures 42 provided in the mounting portion 34, thereby obstructing access to the apertures and the corresponding fasteners extending through the apertures 42 in the support surface 18. By virtue of the installed container 14 covering the apertures 42 and the corresponding fasteners, the bracket 10 cannot be removed from the wall 18 when a container 14 is secured within the bracket 10.

As the securing member 102 pivots toward the second position, the distal end 82 of the second arm portion 62 of the base 30 is received in the aperture 126 defined in the flange 122 of the securing member 102. Additionally, the hook-shaped distal end 134 is received in the aperture 150 of the flange portion 146 of the base 30. Furthermore, the inside edge 118 is received into the groove 26 in the neck 22. With the securing member 102 in the second position, the user can then insert the key into the lock 154 and rotate the key, thereby moving the pawl 158 to the locked position so that it engages both the notch 138 and the slot 162. Once the container 14 is locked within the bracket 10, the user might remove the cover 98 and place it into the aperture 94 so that the container 14 is opened and ready to receive waste.

Any attempts to force the locked bracket 10 open are hampered by the four distinct locations of constrained engagement between the base 30 and the securing member 102, and more specifically at (1) the permanent pivot structure 110, (2) the engagement between the distal end 82 in the aperture 126 in the flange 122, (3) the engagement between the hook-shaped distal end 134 in the aperture 150 in the flange portion 146, and (4) the engagement of the pawl 158 with the notch 138 and the slot 162. Attempts to pry the securing member 102 upwardly, downwardly, or rotationally outwardly relative to the support portion 54 will be impeded or altogether prevented by virtue of the four distinct locations of constrained engagement between the base 30 and the securing member 102.

To open the bracket 10 and remove the container 14 in an authorized manner, the user can insert the key into the lock 154 and rotate the lock and pawl 158 to the unlocked state, in which the pawl 158 rotates out of the slot 162 and clear of the notch 138. The securing member 102 is then free to rotate about the pivot axis 106 in the single pivot plane P to the first position. As this happens, the inside edge 118 will withdraw from within the groove 26 in the neck 22. With the securing member 102 in the first position, the container 14 can be removed from the recess 66 by pulling the container outwardly away from the wall 18 so that the edge 70 withdraws from the groove 26 in the neck 22. Once the container 14 is removed and clear from the bracket 10, the cover 98 can be re-installed onto the container 10. The bracket 10 is then ready to receive a new container 14.

Various features and advantages of the invention are set forth in the following claims.

What is claimed is:

1. A mounting bracket for mounting a container to a support surface, the mounting bracket comprising:
   a base having a mounting portion configured to be mounted to the support surface and a support portion configured to receive a portion of the container;
   a securing member pivotally coupled to the support portion for movement in only a single pivot plane between a first position, in which the container can be removed from the support portion, and a second position, in which the container cannot be removed from the support portion; and
   a lock operable to selectively lock the securing member in the second position, a portion of the lock being movable in a direction orthogonal to the single pivot plane;
   wherein at least one of the base or the securing member includes an aperture through which a portion of an other one of the base or the securing member extends when the securing member is in the second position.

2. The mounting bracket of claim 1, wherein the securing member is fixedly connected to the support portion at a single pivot axis.

3. The mounting bracket of claim 1, wherein the securing member includes a flange defining the aperture through which the portion of the base extends when the securing member is in the second position.

4. The mounting bracket of claim 3, wherein the support portion includes a first arm portion to which the securing member is pivotally coupled, and a second arm portion spaced from the first arm portion to define therebetween a recess into which the portion of the container is received, the second arm portion having a distal end that extends through the aperture in the flange of the securing member when the securing member is in the second position.

5. The mounting bracket of claim 4, wherein the support portion includes a flange defining an aperture through which a portion of the securing member extends when the securing member is in the second position.

6. The mounting bracket of claim 5, wherein the flange is adjacent the second arm portion.

7. The mounting bracket of claim 1, wherein the support portion includes a flange defining the aperture through which the portion of the securing member extends when the securing member is in the second position.

8. The mounting bracket of claim 7, wherein the support portion includes a first arm portion to which the securing member is pivotally coupled, and a second arm portion spaced from the first arm portion to define therebetween a recess into which the portion of the container is received, and wherein the flange is adjacent the second arm portion.

9. The mounting bracket of claim 1, wherein the securing member includes a notch and wherein the lock includes a pawl that selectively engages the notch to lock the securing member in the second position, and disengages the notch to allow the securing member to move out of the second position.

10. The mounting bracket of claim 9, wherein the support portion includes a slot and the pawl extends into the slot when the pawl engages the notch.

11. The mounting bracket of claim 9, wherein the lock is supported in the mounting portion of the base.

12. The mounting bracket of claim 1, wherein each of the base and the securing member have a thickness that permits portions of the base and the securing member to fit within a groove in the container when the securing member is in the second position.

13. The mounting bracket of claim 1, wherein the support portion includes an aperture sized and configured to receive and support a cover of the container when the container is received in the mounting bracket for use.

14. A mounting bracket for mounting a container to a support surface, the mounting bracket comprising:
   a base having a mounting portion configured to be mounted to the support surface and a support portion configured to receive a portion of the container;
   a securing member pivotally coupled to the support portion for movement between a first position, in which the container can be removed from the support portion, and a second position, in which the container cannot be removed from the support portion; and
   a lock operable to selectively lock the securing member in the second position, the lock being a keyed lock in which rotation of a key moves the lock between a locked state and an unlocked state;
   wherein the base includes a flange with an aperture through which a portion of the securing member extends when in the second position; and
   wherein the securing member includes a flange with an aperture through which a portion of the base extends when the securing member is in the second position.

15. The mounting bracket of claim 14, wherein the securing member includes a notch and wherein the lock includes a pawl that selectively engages the notch to lock the securing member in the second position, and disengages the notch to allow the securing member to move out of the second position, and wherein the support portion includes a slot and the pawl extends into the slot when the pawl engages the notch.

16. The mounting bracket of claim 15, wherein the securing member is pivotally coupled to the support portion for movement in only a single pivot plane.

17. A mounting bracket for mounting a container to a support surface, the mounting bracket comprising:
   a base having a mounting portion configured to be mounted to the support surface and a support portion configured to receive a portion of the container;

a securing member pivotally coupled to the support portion between a first position, in which the container can be removed from the support portion, and a second position, in which the container cannot be removed from the support portion; and a lock operable to selectively lock the securing member in the second position;

wherein the securing member includes a notch and wherein the lock includes a pawl that selectively engages the notch to lock the securing member in the second position, and disengages the notch to allow the securing member to move out of the second position; and wherein the support portion includes a slot and wherein the pawl extends into the slot when the pawl engages the notch.

18. The mounting bracket of claim 17, wherein the support portion includes a first arm portion to which the securing member is pivotally coupled, and a second arm portion spaced from the first arm portion to define therebetween a recess into which the portion of the container is received, the second arm portion having a distal end that extends through an aperture in the securing member when the securing member is in the second position.

19. The mounting bracket of claim 17, wherein the support portion includes a first arm portion to which the securing member is pivotally coupled, and a second arm portion spaced from the first arm portion to define therebetween a recess into which the portion of the container is received, wherein the support portion includes an aperture through which a portion of the securing member extends when the securing member is in the second position.

20. The mounting bracket of claim 17, wherein the securing member is pivotally coupled to the support portion for movement in only a single pivot plane.

21. A mounting bracket for mounting a container to a support surface, the mounting bracket comprising:

a base having a mounting portion configured to be mounted to the support surface and a support portion configured to receive a portion of the container, wherein the support portion includes a first arm portion and a second arm portion spaced from the first arm portion to define therebetween a recess into which the portion of the container is received;

a securing member pivotally coupled to the first arm portion of the support portion for movement between a first position, in which the container can be removed from the support portion, and a second position, in which the container cannot be removed from the support portion, wherein the securing member includes a first aperture through which a portion of the base extends when the securing member is in the second position, and wherein the support portion includes a second aperture through which a portion of the securing member extends when the securing member is in the second position; and a lock operable to selectively lock the securing member in the second position;

wherein the securing member includes a notch and wherein the lock includes a pawl that selectively engages the notch to lock the securing member in the second position, and disengages the notch to allow the securing member to move out of the second position; and wherein the support portion includes a slot and wherein the pawl extends into the slot when the pawl engages the notch.

* * * * *